United States Patent [19]

Wegman

[11] Patent Number: 5,218,140
[45] Date of Patent: Jun. 8, 1993

[54] CARBONYLATION REACTION AND CATALYST THEREFOR

[75] Inventor: Richard W. Wegman, South Charleston, W. Va.

[73] Assignee: Union Carbide Chemicals & Plastics Technology Corporation, Danbury, Conn.

[21] Appl. No.: 227,295

[22] Filed: Aug. 2, 1988

[51] Int. Cl.$^5$ .............. C07C 67/36; C07C 67/00; C07C 51/10; C07C 51/12
[52] U.S. Cl. .................. 560/232; 560/204; 562/517; 562/519; 554/13.1
[58] Field of Search ............ 560/232, 204; 260/413, 260/410.9 R; 562/519, 517

[56] References Cited

U.S. PATENT DOCUMENTS 5,026,904 6/1991 Lodge et al. .................. 560/232
5,138,093 8/1992 Rizkalla et al. ................ 560/232

FOREIGN PATENT DOCUMENTS 18927 12/1990 European Pat. Off. .
3323654 1/1985 Fed. Rep. of Germany .
56-104838 8/1981 Japan .
56-104839 8/1981 Japan .
59-139330 8/1984 Japan .
59-172436 9/1984 Japan .

OTHER PUBLICATIONS

Journal of Catalysis 13, p. 106, (1969).
Journal of Catalysis 27, p. 389, (1972).
Krzywicki et al., Bull. Soc. Chim. France 5, p. 1094, (1975).
Krzywicki et al., J. Mol. Cat., 6, p. 431, (1979).
Schwartz et al., J. Mol. Cat., 22, p. 389, (1984).
Gates, J. Mol. Cat., 3, p. 1, (1977).
Tisgdinos, Climax Molybdenum Company, Bulletin Cdb-12a, (1969).
Matveev, et al., J. Mol. Cat., 38, p. 345, (1986).
Dun, et al., Applied Catalysis, 21, p. 61, (1986).
Nomiya, et al., Bull. Chem. Soc. Jap., 53, p. 3719, (1980).
Izumi, et al., J. Mol. Cat., 18, p. 299, (1983).
Moffat, et al., J. of Cat., 77, p. 473, (1982).
Ono, et al., Bull. Chem. Soc. Jap., 55, p. 2657, (1982).
Moffat, et al., J. of Cat., 81, p. 61, (1983).
J. Bailar, Inorganic Synthesis, 1, p. 132, (1939).
L. Baker and T. McCutcheon, J. Am. Chem. Soc., 78, p. 4503, (1956).

Primary Examiner—José G. Dees
Assistant Examiner—Dwayne C. Jones
Attorney, Agent, or Firm—S. H. Hegedus

[57] ABSTRACT

A process and novel catalyst for the carbonylation of one or more of alcohols, ethers and ether alcohols to esters and, optionally, to carboxylic acids. The reaction is effected in the vapor state over a solid catalyst comprising a polyoxometalate anion in which the metal is at least one taken from Group V and VI of the Periodic Chart of the Elements complexed with a cation from a member of Group VIIIA of the Periodic Chart of the Elements. Preferably, the catalyst is deposited on a support that is inert to the reaction. The preferred support is silica.

14 Claims, No Drawings

CARBONYLATION REACTION AND CATALYST THEREFOR

BRIEF DESCRIPTION OF THE INVENTION

Alcohols, ethers and ether alcohols are carbonylated to esters and, optionally, to carboxylic acids, by reaction in the vapor state over a solid catalyst comprising a polyoxometalate anion in which the metal is at least one taken from Group V and VI of the Periodic Chart of the Elements (such as molybdenum, tungsten, vanadium, niobium, chromium, and tantalum), complexed with at least one Group VIIIA (of the Periodic Chart of the Elements) cation, such as Fe, Ru, Os, Co, Rh, Ir, Ni, Pd and Pt. Preferably, the catalyst is deposited on a support that is inert to the reaction. The preferred support is silica. Novel carbonylation catalysts are described.

BACKGROUND TO THE INVENTION

Carbonylation of alcohols and ethers to their corresponding esters is a well known art and is illustrated in Equations 1 and 2 below.

$$2ROH + CO \rightarrow RC(O)OR + H_2O \quad (1)$$

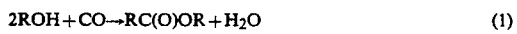

$$ROR' + CO \rightarrow RC(O)OR' \quad (2)$$

In addition, alcohols can be carbonylated to carboxylic acids as shown in Equation 3, below.

$$ROH + CO \rightarrow RC(O)OH \quad (3)$$

Carbonylation of methanol, equations 1 and 3, is a well known reaction and is traditionally carried out in the liquid phase with a catalyst. The catalyst typically comprises a Group VIII metal, a halide promoter (normally some form of iodide) and occasionally a ligand such as $PR_3$ or $NR_3$ (R being organic moiety).

The most common catalyst for a liquid phase system is Rh in combination with $HI/CH_3I$. This catalyst is considered "state of the art" and is described in U.S. Pat. No. 3,769,329. This technology/catalyst is utilized in many commercial processes that generate acetic acid via methanol carbonylation. The operating conditions are about 180°–200° C. and about 450 psi CO with >95% selectivity to methyl acetate/acetic acid.

Prior to the development of the Rh and $HI/CH_3I$ system, the reaction was carried out in a liquid phase system with Co-I catalysts such as described in U.S. Pat. No. 3,060,233. The operating conditions are about 200° C. and about 7,000–10,000 psi CO. The product selectivity is about 93%. A number of researchers have described the use of Ni-based catalysts for the carbonylation reaction. An example is EP 18 927. The catalyst of that publication consists of Ni and a combination of ionic iodides (example: KI) and covalent iodides (example: $CH_3I$). The reaction is carried out at about 150° C. and about 800–1,000 psi CO.

All of the liquid phase catalysts that generate methyl acetate/acetic acid at commercially acceptable rates and selectivities require the use of an iodide promoter, typically $CH_3I$ and/or HI, and high pressure (at least about 450 psi). The iodides are highly corrosive and necessitate the use of expensive corrosion resistant materials of construction. In addition, separation of the catalyst is a major problem and requires special equipment.

Vapor phase carbonylation of methanol has the advantage of easy product separation from the catalyst. In most cases, patents describing homogeneous catalysts also claim that the reaction can be carried out in the vapor phase [e.g., methanol and an iodide containing compound ($CH_3I$) are co-fed] with the catalyst supported on a material such as silica ($SiO_2$) or alumina ($Al_2O_3$). Rarely are examples given. The following descriptions refer to references which deal only with vapor phase carbonylation.

A considerable amount of work has been carried out on heterogeneous versions of the $Rh/CH_3I$ system described above, see for example, *Journal of Catalysis* (13, p. 106, 1969 and 27, p. 389, 1972). In a typical illustration, Rh is supported on activated carbon and a gaseous mixture of CO, $CH_3OH$, and $CH_3I$ is passed over the catalyst at 175°–250° C. and 300 psi. The catalyst is active and high yields of acetic acid/methyl acetate are obtained. In similar work, Rh is impregnated on $Al_2O_3$ (Krzywicki et. al., *Bull. Soc. Chim. France*, 5, p. 1094, 1975), $SiO_2$ and $TiO_2$ (Krzywicki et.al., *J. Mol. Cat.*, 6, p. 431, 1979) or zeolite-encapsulated (Schwartz et.al., *J. Mol. Cat.*, 22, p. 389, 1984). In both cases $CH_3OH$ and $CH_3I$ are co-fed to the reactor containing the catalyst. It should be noted that in all these examples $CH_3I$ is required in order for the carbonylation reaction to work.

In JA 59139330, the carbonylation catalyst consist of Ni supported on activated carbon. The reaction is carried out at 200°–300° C. and 150 psi with a feed mixture of $CO:CH_3OH:CH_3I = 5:1:0.01$. At 300° C., the methanol conversion is 100% and the acetic acid/methyl acetate selectivity is >95%. In JA 59172436 the same catalyst is utilized to carbonylate dimethyl ether. In DE 3323654 a $CH_3OH/CH_3I$ feed mixture is carbonylated with a Pd-Ni catalyst supported on activated carbon. The reaction is carried out at 300° C. and 1 atm CO.

Gates, *J. Mol. Cat.*, 3, p. 1, 1977, reports that Rh impregnated in crosslinked polystyrene is a vapor phase catalyst for the carbonylation of $CH_3OH$. Catalyst activity and stability are low. In JA 56104838 and JA 56104839 various Group VIII metals (Rh, Ni, Pd, Ru, Co) and rare earth metal oxides (Cs, La) are supported on silica. Methanol carbonylation is carried out at 150°–200° C. and 1–5 atm CO, and methyl acetate selectivity is high. In these examples, $CH_3I$ is not utilized in the reaction feed.

Vapor phase processes that need $CH_3I$ as a promoter will be corrosive and require expensive materials of construction. In addition, extensive separation/purification procedures are required in order to remove iodides from the product.

Heteropoly acids are well known compounds. The name "heteropoly acids" refers to a broad class of compounds of varying composition. A good general review of their physical properties is given by Tisgdinos in Climax Molybdenum Company, Bulletin Cdb-12a, 1969.

The use of heteropoly acids in many areas of catalysis is well known including dehydration of alcohols, Friedel-Crafts type reactions, oxidative dehydrogenation and partial oxidation of organic compounds. For examples see Matveev, et. al., *J. Mol. Cat.*, 38, 345, 1986, Dun, et. al., *Applied Catalysis*, 21, 61, 1986, Nomiya, et. al., *Bull. Chem. Soc. Jap.*, 53, 3719, 1980, and Izumi, et. al. *J. Mol. Cat.*, 18, 299, 1983. Recently, much attention has been given to heteropoly acids as a catalyst for the conversion of methanol into hydrocarbons:

$$xCH_3OH \rightarrow CH_2=CH_2 + CH_3CH=CH_2 + \text{other hydrocarbons} \quad (4)$$

See Moffat, et. al., *J. of Cat.*, 77, p. 473, 1982, Ono, et. al. *Bull. Chem. Soc. Jap.*, 55, p. 2657, 1982, and Moffat, et.al., *J. of Cat.*, 81, p. 61, 1983. This reaction is carried out in the vapor phase (300°-375° C.) and the products include ethylene, propylene and saturated $C_{1-5}$ hydrocarbons. Reaction 4 dominates the known chemistry of reactions of methanol in the presence of heteropoly acids. It was therefore unexpected to find that methanol carbonylation could be carried out with heteropoly acids.

Hetero polyacids and polyoxometalate anions constitute well recognized compositions. They embrace the well-known complexes called isopolyoxoanions and heteropolyoxoanions. They are represented by the general formulas[1]

1. See Pope, Heteropoly and Isopoly Oxometalates, Published by Springer-Verlag, Berlin, 1983, page 1.

$[M_mO_y]^{p-}$    Isopolyanions
$[X_xM_mO_y]^{q-}$   Heteropolyanions
$(x \leq m)$ wherein M is at least one metal taken from Group V and VI of the Periodic Chart of the Elements (such as molybdenum, tungsten, vanadium, niobium, chromium, and tantalum) in their highest ($d^0$, $d^1$) oxidation states, and X is a heteroatom from all groups of the Periodic Chart of the Elements with the possible exception of the rare gases.[2]

2. Pope, supra, page 2, takes the position that the "terms polyoxometalate or or polyoxoanion might be therefore more appropriate to describe the field."

THE INVENTION

This invention relates to a novel vapor phase carbonylation process of alcohols and ethers which utilizes polyoxometalate anions as the catalysts and to the catalysts. The process involves the carbonylation of one or more of alcohols, ethers, and ether alcohols to esters and, optionally, to carboxylic acids, by reaction thereof in the vapor state over a solid catalyst comprising a polyoxometalate anion in which the metal is at least one taken from Group V and VI of the Periodic Chart of the Elements complexed with a cation from a member of Group VIIIA of the Periodic Chart of the Elements.

The process of the invention, in a preferred embodiment, involves the carbonylation of one or more of alcohols, such as mono- and polyhydric alcohols, alkylethers, such as alkyl or alkylene mono- and polyethers, and alkyl ether alcohols to alkyl alkane monoesters and diesters and, optionally, to alkane monocarboxylic or dicarboxylic acids, by reaction in the vapor state over a solid catalyst comprising a polyoxometalate anion in which the metal is at least one taken from Group V and VI of the Periodic Chart of the Elements (such as molybdenum, tungsten, vanadium, niobium, chromium, and tantalum), complexed with at least one Group VIIIA (of the Periodic Chart of the Elements) cation, such as Fe, Ru, Os, Co, Rh, Ir, Ni, Pd and Pt. Preferably, the catalyst is deposited on a support that is inert to the reaction. The preferred support is silica.

The invention also embraces solid catalysts for the carbonylation of one or more of alcohols, ethers and ether alcohols to esters and, optionally, to carboxylic acids, by reaction thereof in the vapor state. The carbonylation catalysts comprise a polyoxometalate anion in which the metal is at least one taken from Group V and VI of the Periodic Chart of the Elements (such as molybdenum, tungsten, vanadium, niobium, chromium, and tantalum), complexed with at least one Group VIIIA (of the Periodic Chart of the Elements) cation, such as Fe, Ru, Os, Co, Rh, Ir, Ni, Pd and Pt. The preferred catalyst is deposited on a support which is inert to the reaction. The preferred support is silica, especially a high surface area silica.

DETAILS OF THE INVENTION

The invention is directed to a process of converting alcohols and ethers to carboxylic acids and esters by the carbonylation of the alcohols and ethers with carbon monoxide in the presence of a metal ion exchanged heteropoly acid supported on an inert support. The invention also embraces novel carbonylation catalysts.

The alcohols and ethers that may be carbonylated by the process of the invention include any alcohol and ether compound or combination of the two. They are preferably exemplified by alcohols and ethers in which an aliphatic carbon atom is directly bonded to an oxygen atom of either an alcoholic hydroxyl group in the compound or an ether oxygen in the compound. Such compounds may contain aromatic groups.

The preferred alcohols and ethers that may be carbonylated by the process of the invention include alkanols of 1 to about 20 carbon atoms, alkane polyols of 2 to about 24 carbon atoms, alkyl monoethers of 2 to about 20 carbon atoms, alkyl alkylene polyethers of 4 to about 40 carbon atoms and alkoxyalkanols of 3 to about 20 carbon atoms.

Illustrative of suitable alcohols and ethers that may be carbonylated according to the process of the invention are:

| | |
|---|---|
| $CH_3OH$ | $CH_3CH_2OH$ |
| $CH_3CH_2CH_2OH$ | $CH_3CH(OH)CH_3$ |
| $CH_3CH_2CH_2CH_2OH$ | $CH_3CH_2(CH_3)CHOH$ |
| $CH_3(CH_3)CHCH_2OH$ | $CH_3CH_2CH_2CH_2CH_2OH$ |
| $CH_3CH_2CH_2CH(OH)CH_3$ | $CH_3CH_2CH(OH)CH_2CH_3$ |
| $CH_3CH_2CH(OH)CH_2CH_3$ | $CH_3(CH_3)C(OH)CH_2CH_3$ |
| $CH_3(CH_3)CHCH(OH)CH_3$ | $CH_3CH_2CH_2CH_2CH_2CH_2OH$ |
| $CH_3CH_2CH_2CH_2CH(OH)CH_3$ | $CH_3CH_2CH_2CH(OH)CH_2CH_3$ |
| $CH_3CH_2CH_2(CH_3)CHCH_2OH$ | $CH_3CH_2(CH_3)CHCH_2CH_2OH$ |
| $CH_3CH_2(CH_3CH_2)CHCH_2OH$ | $CH_3(CH_3CH_2)CHCH_2CH_2OH$ |
| $CH_3(CH_2)_8OH$ | $CH_3(CH_2)_{17}OH$ |
| $CH_3(CH_2)_8(CH_3)CH_2OH$ | $C_6H_{11}OH$ |
| $C_6H_{11}CH_2OH$ | $C_6H_5CH_2OH$ |
| $o\text{-}C_6H_5(CH_2OH)_2$ | $p\text{-}C_6H_5(CH_2OH)_2$ |
| $1,2,4\text{-}C_6H_5(CH_2OH)_3$ | $p\text{-}C_6H_5(CH_2CH_2OH)_2$ |
| $HOCH_2CH_2OH$ | $HOCH_2CH_2CH_2OH$ |
| $HOCH_2CH_2CH_2CH_2OH$ | $HO(CH_2)_{4-17}CH_2OH$ |
| $(HOCH_2)_4C$ | $1,4\text{-}HOC_6H_4CH_2OH$ |
| $CH_3OCH_3$ | $CH_3CH_2OCH_3$ |

| -continued | |
|---|---|
| CH₃CH₂OCH₂CH₃ | CH₃CH₂CH₂OCH₃ |
| CH₃CH₂CH₂OCH₂CH₃ | CH₃CH₂CH₂OCH₂CH₂CH₃ |
| CH₃CH(OCH₃)CH₃ | CH₃CH₂CH₂CH₂OCH₃ |
| CH₃CH₂(CH₃)CHOCH₃ | CH₃(CH₃)CHCH₂OCH₂CH₃ |
| CH₃CH₂CH₂CH₂CH₂OCH₃ | CH₃CH₂CH₂CH(OCH₂CH₂OCH₃)CH₃ |
| CH₃CH₂CH(OCH₃)CH₂CH₃ | CH₃CH₂CH(OCH₂CH₃)CH₂CH₃ |
| CH₃(CH₃)C(OCH₂CH₃)CH₂CH₃ | CH₃(CH₃)CHCH(OCH₂CH₂OCH₂CH₃)CH₃ |
| CH₃CH₂CH₂CH₂CH₂OCH₃ | CH₃CH₂CH₂CH₂CH(OCH₃)CH₃ |
| CH₃CH₂CH₂CH(OCH₃)CH₂CH₃ | CH₃CH₂CH₂(CH₃)CHCH₂OCH₃ |
| CH₃CH₂(CH₃)CHCH₂CH₂OCH₃ | CH₃CH₂(CH₃CH₂)CHCH₂OCH₃ |
| CH₃(CH₃CH₂)CHCH₂CH₂OCH₃ | CH₃(CH₂)₈OCH₃ |
| CH₃(CH₂)₁₇OCH₃ | CH₃(CH₂)₈(CH₃)CH₂OCH₃ |
| C₆H₁₁OCH₃ | C₆H₁₁OC₆H₁₁ |
| C₆H₁₁CH₂OC₆H₅ | C₆H₅OCH₃ |
| C₆H₅OH | C₆H₅CH₂OCH₃ |
| o-C₆H₅(CH₂OCH₃)₂ | p-C₆H₅(CH₂OCH₃)₂ |
| 1,2,4-C₆H₅(CH₂OCH₃)₃ | CH₃(OCH₂CH₂)₁₋₃₀OCH₃ |
| C₆H₅CH₂OCH₂CH₂CH₂OH | CH₃OCH₂CH₂CH₂CH₂OH |
| CH₃O(CH₂)₄₋₁₇CH₂OH | (CH₃OCH₂)₄C |
| sym-CH₃OC₆H₄CH₂OH | CH₃(OCH₂CH₂)₁₋₃₀OH |
| (CH₃OCH₂)₂(HOCH₂)₂C | 1,4-CH₃OCH₂C₆H₄CH₂OCH₃ |

The process of the invention involves providing the alcohol and/ether in the vapor state and passing the vapor over a bed containing the solid catalyst comprising a polyoxometalate anion in which the metal is at least one taken from Group V and VI of the Periodic Chart of the Elements (such as molybdenum, tungsten, vanadium, niobium, chromium, and tantalum), complexed with at least one Group VIIIA (of the Periodic Chart of the Elements) cation, such as Fe, Ru, Os, Co, Rh, Ir, Ni, Pd and Pt. The temperature at which the reaction is effected is not seen to be narrowly critical. A temperature between about 100° C. and about 350° C. is usable. Preferably, the temperature of the reaction is between about 125° C. and about 325° C., and temperatures between about 150° C. and about 300° C. are most preferred.

The reaction pressure accommodates the requirement that the reactants be fed to the reactor in the vapor state. However, the pressure at which the reaction may be carried out may range from about 1 atmosphere to about 1,000 atmospheres, with pressures of greater than 1 atmosphere to about 35 atmosphere being preferred. The particular reactants and the rate of reaction will impact on the pressure of the reaction zone.

The reaction zone is where the catalyst is located. The reaction may be carried out in a tubular reactor using a fixed bed of the catalyst. The reactants may be fed to the catalyst by feeding down or up, or a combination of both, to a fixed bed located in an upright tubular reactor. It is preferred to use a reactor design that operates by plug flow and causes the minimal turbulence in the reaction zone. The reaction may be effected in a dynamic bed of the catalyst. In such a reaction, the bed of catalyst is moving such as in the case of a fluid bed of the catalyst.

The gas hourly space velocity[3] of the reactants through the reaction zone may be over a broad range. For example, the GHSV may range from about 50 to about 50,000 hr.⁻¹, preferably from about 900 to about 25,000 hr.⁻¹ The liquid hourly space velocity[4] to the reactor when the feed is vaporized within the reactor may range from about 0.01 to about 10 hr.⁻¹

[3]. GHSV—gas hourly space velocity. This is the rate of gas flow over the catalyst. It is determined by dividing the volume of gas (at 25° C. and 1 atm.) which passes over the catalyst in one hour by the volume of the catalyst.
[4]. LHSV—liquid hourly space velocity. This is the rate that the liquid organic substrate is fed to the reactor. It is determined by dividing the liquid volume pumped in one hour by the volume of catalyst.

Where the alcohol, ether and/or the ether alcohol reactant is a higher boiling material not easily vaporized it can be diluted with a lower boiling nonreactive solvent or diluent and thus transported over the solid catalyst. The degree of dilution in some cases can be quite extreme and of course, such conditions will adversely affect the cost of carbonylation. Suitable solvents and diluents include aliphatic and aromatic hydrocarbons, halogenated hydrocarbons, esters, ketones, and the like.

The invention involves a new family of catalysts for carrying out the carbonylation reactions herein described such as the carbonylation of methanol or dimethyl ether to methyl acetate/acetic acid. The general formula of a preferred form of the heteropoly acid used in the practice of the invention is $M[Q_{12}PO_{40}]$ where M is a Group VIII metal or a combination of Group VIII metals, Q is one or more of tungsten, molybdenum, vanadium, niobium, chromium, and tantalum, P is phosphorus, and O is oxygen. In a particularly preferred embodiment of the invention, Q is tungsten or molybdenum or a mixture of the two. The preferred catalyst is derived from heteropoly acids of the formula $H_3W_{12}PO_{40} \cdot xH_2O$. They are acids and generate $H^+$.

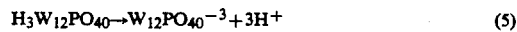  (5)

The preferred catalysts comprise metal ion exchanged heteropoly acids of the general formula $M[W_{12}PO_{40}]$ where M is as defined above, W is tungsten, and P and O are as defined above supported on a $SiO_2$ support. The carbonylation reaction is carried out in the vapor phase. A wide variety of catalysts were screened. The preferred catalysts are those where M is Rh, Rh/Pd combinations, Ir, Ir/Rh combinations, Ir/Pd combinations and Ir/Co combinations.

$H_3W_{12}PO_{40}$ can be chemically modified in several ways. The most straight forward approach is to exchange the acidic protons with a metal ion:

  (6)

Any metal ion $M^+$ or a combination of ions capable of satisfying the heteropoly acid valence requirements can be utilized. Removal of all of the $H^+$ is not required. For example, the reaction with $Co^{+2}$ would yield:

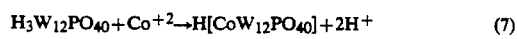  (7)

These catalyst compositions are based on idealized stoichiometries such as that shown by equation (7) immediately above. The exact structure and composition of the ultimate catalyst (i.e., the composition effecting the catalytic activity as contrasted with the starting heteropoly acid) is not known. The catalyst structure may exist as monomers, dimers and so forth. The waters of hydration are not known and are not included in the catalyst formulas.

All of the $M[W_{12}PO_{40}]/SiO_2$ catalysts utilized herein as catalyst precursors were prepared in a similar manner, a typical example is as follows:

Under $N_2$ at room temperature, $RhCl_3 \cdot H_2O$ (0.47 g., 1.8 mmoles) was dissolved in 50 milliliters of methanol and stirred for 0.5 hr. $H_3W_{12}PO_{40}$ (15-20 wt. % water, 6.5 g., 1.8 mmoles) was added and this solution was stirred for 1.0 hour. To the solution was added 3.9 g. of grade 12 silica gel ($SiO_2$) and the resulting slurry was stirred for an additional 4.0 hours. The methanol was then removed at 80° C. under vacuum yielding a red powder. If needed, the flask was further heated with a heat gun until the powder was free flowing. The material was placed in a vial and stored under $N_2$. The empirical formula of the composition is $Rh[W_{12}PO_{40}]/SiO_2$.

Some of the $M[W_{12}PO_{40}]$ catalysts were prepared with metal nitrate salts. No difference in catalytic activity was seen between $Rh[W_{12}PO_{40}]$ prepared from chloride, nitrate or AcAc (acetylacetonate) containing Rh salts. $H_3[Mo_xW_yPO_{40}]$ acids were prepared by the procedure of J. Bailar, *Inorganic Synthesis*, 1, p. 132, (1939) and $Na_8[Rh_2W_{12}O_{42}]$ was prepared by procedures analogous to $Na_8[Co_2W_{12}O_{42}]$ as reported by L. Baker and T. McCutcheon, *J. Am. Chem. Soc.*, 78, p. 4503, (1956).

As illustrated above, the heteropoly acid is impregnated on the support using conventional procedures. The choice of the support is not appreciated to be limiting factor in the operation of the invention. The limited experience with the selection of supports relative to the supports effect on the activity of the catalyst suggests that the support should have a reasonably high surface area. It is preferred that the heteropoly acid be deposited on an inorganic support that has a relatively high surface area, such as a surface area of at least about 100 square meters per gram determined by the BET method. In the preferred embodiment of the invention, the surface area of the support onto which the heteropoly acid is deposited, and in contact with, has a surface area of at least about 200 square meter per gram, most preferably at least about 250 square meter per gram. Typical support materials suitable for the invention are the silicas, the gamma-aluminas, the titanias, the alumina silicates, the high surface area clays, and the like. Particularly desirable are the mixed composite supports in which the high surface area support is deposited over a lower surface area support. For example, a silica gel deposited and cured on the surface of an alpha-alumina provides the high surface area for the subsequent deposition of the heteropoly acid onto the silica gel coating and the thermal stability provided by the low surface area alpha-alumina.

The impregnation step simply involves the coating of the support with the heteropoly acid and then drying the coating on the support to fix it. The drying temperature is not narrowly critical and can range from about 100° C. to about 600° C. for a period of about 5 seconds to about 8 hours. The lower the temperature, the longer will be the heating period and the higher the temperature, the shorter will be the heating period.

The most commercially interesting reactants are methanol and dimethyl ether. The products are methyl acetate and acetic acid. The methyl acetate selectivity can be at least 95% at 225° C. and 1 atm. total operating pressure.

$$2CH_3OH + CO \rightarrow CH_3C(O)OCH_3 + H_2O \qquad (8)$$

$$CH_3OCH_3 + CO \rightarrow CH_3C(O)OCH_3 \qquad (9)$$

In addition, methanol can be carbonylated to acetic acid as shown in Equation 10, below.

$$ROH + CO \rightarrow RC(O)OH \qquad (10)$$

In the case of the carbonylation of methanol, dehydration occurs as a side reaction due to the acidic nature of the heteropoly acid catalysts of the invention, e.g., the $M[W_{12}PO_{40}]$ catalysts. Dehydration results in the formation of dimethyl ether as shown by equation 11.

$$2CH_3OH \rightarrow CH_3OCH_3 + H_2O \qquad (11)$$

Since dimethyl ether is carbonylated to methyl acetate (equation 6) it can be recycled back to the reactor with no loss in methanol efficiency. Thus, the feed to the reactor can comprise methanol, dimethyl ether or a combination of both.

In the examples which follow, the GHSV=900 $hr^1$ and the LHSV=0.15 $hr^1$. The reactor was a clean $\frac{1}{4}''$ stainless steel tube packed with glass wool, 2 milliliter of catalyst and additional glass wool. The tube was placed in an aluminum block surrounded by a heater and connected to the feed and exit lines. The CO flow was started, the temperature of the feed/exit lines adjusted to 160° C. and the reactor taken to the desired temperature. At temperature the methanol feed was started and the system was allowed to equilibrate 0.5 hr. Each experiment was normally carried out for 6 hr. The gas stream exiting the reactor was analyzed with a HP 5830 gas chromatograph equipped with a TC detector and a $10' \times \frac{1}{8}''$ column packed with Poropak Super Q. The following program was used: temp 1=50° C., time 1=0 min., rate=15 degrees/min., temp 2=225° C., time 2=20 min.

EXAMPLES 1-9

The various $MW_{12}PO_{40}/SiO_2$ compounds listed in Table 1 below were prepared on a silica support having a surface area of about 683 $m^2$/gram according to the procedure described above and examined as catalysts for the carbonylation of methanol. The experiments were carried out at 225° C. and 1 atm. with LHSV=0.15 $hr^{-1}$ and GHSV=900 $hr^{-1}$. The results are listed in Table 1. The reported catalyst compositions are idealized stoichiometries.

TABLE 1

| | | Product Yield | | |
|---|---|---|---|---|
| Ex. No. | Catalyst | MeOH | DME | MeOAc |
| 1 | $IrW_{12}PO_{40}$ | 8.0 | 52.0 | 40.0 |
| 2 | $RhW_{12}PO_{40}$ | 17.0 | 49.0 | 34.0 |
| 3 | $HPdW_{12}PO_{40}$ | 0.0 | 92.0 | 8.0 |
| 4 | $HMnW_{12}PO_{40}$ | 0.0 | 96.0 | 4.0 |
| 5 | $HCoW_{12}PO_{40}$ | 5.0 | 92.0 | 3.0 |
| 6 | $HNiW_{12}PO_{40}$ | 7.0 | 90.0 | 3.0 |
| 7 | $FeW_{12}PO_{40}$ | 7.0 | 92.0 | 1.0 |
| 8 | $HZnW_{12}PO_{40}$ | 0.0 | 99.0 | 1.0 |

TABLE 1-continued

| Ex. No. | Catalyst | Product Yield | | |
|---|---|---|---|---|
| | | MeOH | DME | MeOAc |
| 9 | ThW$_{12}$PO$_{40}$ | 6.0 | 93.0 | 1.0 |

EXAMPLE 10

The catalyst of Example 2 (RhW$_{12}$PO$_{40}$) was supported on alumina, florisil, and alundum supports instead of SiO$_2$. The carbonylation reaction was carried out exactly as Examples 1-9. Small amounts of methyl acetate were formed.

EXAMPLES 11-18

Bimetallic compounds, M1M2W$_{12}$PO$_{40}$ deposited on SiO$_2$, where M1M2 is a combination of two metals (M1+M2), were examined as catalysts. The catalysts were prepared such that the mole ratio of M1:M2:H$_3$W$_{12}$PO$_{40}$=1:1:2. The exact composition of these materials was not determined. The carbonylation reaction was carried out as described in Examples 1-9. The results are given in Table 2 below.

TABLE 2

| Ex. No. | M1 | M2 | Product Yield | | |
|---|---|---|---|---|---|
| | | | MeOH | DME | MeOAc |
| 11 | Rh | Ir | 4.0 | 52.0 | 44.0 |
| 12 | Rh | Mn | 3.0 | 62.0 | 35.0 |
| 13 | Rh | Pd | 3.0 | 38.0 | 59.0 |
| 14 | Rh | Co | 6.0 | 68.0 | 26.0 |
| 15 | Ir | Co | 3.0 | 39.0 | 58.0 |
| 16 | Ir | Mn | 5.0 | 41.0 | 54.0 |
| 17 | Ir | Pd | 2.0 | 40.0 | 58.0 |
| 18 | Pd | Mn | 8.0 | 84.0 | 8.0 |

EXAMPLES 19-23

In these example, Na$_8$[Rh$_2$W$_{12}$O$_{42}$] without deposition on silica support (catalyst "A") and deposited on silica support (catalyst "B") were examined as carbonylation catalysts. The runs were carried out similar to Example 1-9. The results are reported in Table 3 below.

TABLE 3

| Ex. No. | Catalyst | Temp. °C. | Product Yield | | |
|---|---|---|---|---|---|
| | | | MeOH | DME | MeOAc |
| 19 | A | 225 | 99.0 | 0.0 | 1.0 |
| 20 | A | 250 | 98.0 | 0.0 | 2.0 |
| 21 | A | 275 | 96.0 | 0.0 | 4.0 |
| 22 | B | 225 | 87.0 | 0.0 | 13.0 |
| 23 | B | 275 | 85 | 0.0 | 15.0 |

EXAMPLES 24-27

Heteropoly acids containing both W and Mo were synthesized according to the following reaction:

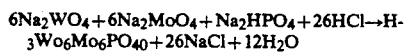

The reaction is general therefore H$_3$W$_x$Mo$_y$PO$_{40}$, where x+y=12, were prepared by adjusting the ratios of the reagents. The H$_3$W$_x$Mo$_y$PO$_{40}$ acids were then exchanged with Rh and deposited onto SiO$_2$ to give RhW$_x$Mo$_y$PO$_{40}$/SiO$_2$ catalysts. The catalysts were examined at 225° C., 1 atm CO and GHSV=900 hr$^{-1}$. The results are given in Table 4 below.

TABLE 4

| Example No. | Catalyst RhW$_x$Mo$_y$PO$_{40}$ | | MeOAc Yield % |
|---|---|---|---|
| | x | y | |
| 24 | 8 | 4 | 16.0 |
| 25 | 6 | 6 | 11.0 |
| 26 | 4 | 8 | 8.0 |
| 27 | 2 | 10 | 4.0 |

EXAMPLES 28-33

In these examples methanol was replaced by dimethyl ether. The reaction was carried out at 225° C. and 1 atm. CO with the catalysts reported in Table 5 below. Each of the catalysts were deposited and supported on high surface area silica, as characterized above.

TABLE 5

| Ex. No. | Catalyst | Product Yield | | |
|---|---|---|---|---|
| | | MeOH | DME | MeOAc |
| 28 | IrW$_{12}$PO$_{40}$ | 0.0 | 87.0 | 13.0 |
| 29 | RhW$_{12}$PO$_{40}$ | 0.0 | 84.0 | 16.0 |
| 30 | HCoW$_{12}$PO$_{40}$ | 1.0 | 98.0 | 1.0 |
| 31 | HNiW$_{12}$PO$_{40}$ | 2.0 | 96.0 | 1.0 |
| 32 | Ir—Pd[W$_{12}$PO$_{40}$]$^5$ | 0.0 | 89.0 | 11.0 |
| 33 | Rh—Pd[W$_{12}$PO$_{40}$]$^6$ | 0.0 | 99.0 | 1.0 |

In the above:
1. "Me" stands for methyl and "Ac" stands for acetate.
2. "Product yield": Unless otherwise noted, the only products observed in the off gas stream were methanol (MeOH), dimethyl ether (DME), and methyl acetate (MeOAc). The product yield for each component is given by
Product Yield = P/Combined weight of MeOH + MeOAc + DME
where P is the weight of methanol, methyl acetate or dimethyl ether. Note that this is not product selectivity. Since methanol and dimethyl ether can be recycled back to methyl acetate the selectivity to methyl acetate approaches 100%.
$^5$Same catalyst as used in Example 17 above.
$^6$Same catalyst as used in Example 13 above.

I claim:

1. A process for the carbonylation of one or more alcohols, ethers and ether alcohols to esters and, optionally, to carboxylic acids, by reaction thereof in the vapor state over a solid catalyst comprising a polyoxometalate anion in which the metal is one or more metals selected from the group consisting of molybdenum, tungsten, vanadium, niobium, chromium, and tantalum, complexed with a cation of one or more metals selected from the group consisting of Fe, Ru, Os, Co, Rh, Ir, Ni, Pd and Pt.

2. The process of claim 1 wherein the catalyst is deposited on a support that is inert to the reaction.

3. The process of claim 2 wherein the support is a member of the group consisting of silicas, the gamma-aluminas, the titanias, the alumina silicates, and the high surface area clays.

4. The process of claim 2 wherein the support is a mixed composite supports in which a high surface area support is deposited over a lower surface area support.

5. The process of claim 4 wherein the support is silica.

6. The process of claim 5 wherein the alcohol is methanol.

7. The process of claim 5 wherein the ether is dimethyl ether.

8. The process of claim 5 wherein the ester is methyl acetate.

9. The process of claim 5 wherein the surface area of the silica is at least about 100 square meters per gram.

10. The process of claim 5 wherein the surface area of the silica is at least 200 square meter per gram.

11. The process of claim 5 wherein the surface area of the silica is at least 250 square meter per gram.

12. The process of claim 1 wherein the temperature of the reaction is about 100° C. to about 350° C.

13. The process of claim 2 wherein the temperature of the reaction is about 100° C. to about 350° C.

14. The process of claim 5 wherein the temperature of the reaction is about 100° C. to about 350° C.

* * * * *